US012697469B2

(12) United States Patent
Lauer et al.

(10) Patent No.: US 12,697,469 B2
(45) Date of Patent: Aug. 4, 2026

(54) IV CATHETER INSERTION GUIDE

(71) Applicant: Becton, Dickinson and Company, Franklin Lakes, NJ (US)

(72) Inventors: Shaun Lauer, Salt Lake City, UT (US); Rajakumar Nallaswamy, Draper, UT (US); Mitchell Wheat, Sandy, UT (US); Rachel Molloy, Sandy, UT (US); John Lackey, West Valley City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 833 days.

(21) Appl. No.: 17/497,708

(22) Filed: Oct. 8, 2021

(65) Prior Publication Data

US 2022/0134059 A1      May 5, 2022

Related U.S. Application Data

(60) Provisional application No. 63/107,342, filed on Oct. 29, 2020.

(51) Int. Cl.
*A61N 7/00*        (2006.01)
*A61M 25/01*       (2006.01)
          (Continued)

(52) U.S. Cl.
CPC ........ *A61M 25/0612* (2013.01); *A61M 25/01* (2013.01); *A61M 25/02* (2013.01);
          (Continued)

(58) Field of Classification Search
CPC .............. A61M 25/0612; A61M 25/02; A61M 25/0606; A61M 2209/088; A61M 25/01;
          (Continued)

(56) References Cited

U.S. PATENT DOCUMENTS

| | | | | | |
|---|---|---|---|---|---|
| 3,135,263 | A | * | 6/1964 | Connelley, Jr. ........ | A61B 90/11 378/162 |
| 3,620,209 | A | * | 11/1971 | Kravitz ................. | A61M 5/422 601/79 |

(Continued)

FOREIGN PATENT DOCUMENTS

| | | |
|---|---|---|
| CN | 101171046 A | 4/2008 |
| CN | 216725475 U | 6/2022 |

(Continued)

*Primary Examiner* — Theodore J Stigell
*Assistant Examiner* — Benjamin Koo
(74) *Attorney, Agent, or Firm* — Kirton McConkie; Whitney Blair; Kevin Stinger

(57) ABSTRACT

An IV catheter insertion guide is configured to reduce the pain a patient may experience during catheter insertion. The IV catheter insertion guide may include two platforms that can be positioned on opposing sides of the insertion site. An upstream platform can include an ultrasonic transducer or another type of heating component for increasing the temperature of tissue near the insertion site. This heating of the tissue can cause the targeted vessel to relax and increase its cross-sectional area prior to insertion of the catheter. A downstream platform can also include an ultrasonic transducer for stimulating nerves downstream from the insertion site during the insertion of the catheter. The stimulation of the downstream nerves may reduce the pain signal that is transmitted to the central nervous system in response to the catheter insertion.

16 Claims, 6 Drawing Sheets

(51) Int. Cl.
*A61M 25/02*        (2006.01)
*A61M 25/06*        (2006.01)

(52) U.S. Cl.
CPC ........... *A61M 25/0606* (2013.01); *A61N 7/00* (2013.01); *A61M 2025/0253* (2013.01); *A61M 2209/088* (2013.01); *A61N 2007/0021* (2013.01); *A61N 2007/0026* (2013.01)

(58) Field of Classification Search
CPC ...... A61M 5/158; A61M 5/422; A61M 21/00; A61M 2005/1585; A61M 2025/028; A61M 2205/3653; A61M 2205/368; A61M 2205/3693; A61M 2210/12; A61M 2205/058; A61M 2205/587; A61M 5/427; A61M 2017/3405; A61N 7/00; A61N 2007/0021; A61N 2007/0026; A61N 7/02; A61F 2007/0285; A61F 7/007; A61B 2017/0073; A61B 5/15003; A61B 5/150106; A61B 5/150122; A61B 5/150137; A61B 5/153; A61B 5/150748; A61B 2017/3407
See application file for complete search history.

(56) References Cited

U.S. PATENT DOCUMENTS

| | | | | |
|---|---|---|---|---|
| 4,883,053 | A * | 11/1989 | Simon ................ | A61B 17/3403 604/116 |
| 6,752,812 | B1 * | 6/2004 | Truwit ................... | A61B 90/11 606/1 |
| 9,044,542 | B2 | 6/2015 | Patrick et al. | |
| 2005/0070819 | A1 * | 3/2005 | Poux ............... | A61B 5/150099 600/576 |
| 2007/0161907 | A1 | 7/2007 | Goldman et al. | |
| 2008/0139974 | A1 * | 6/2008 | Da Silva ............... | A61B 8/546 601/3 |
| 2008/0255483 | A1 * | 10/2008 | Goldberg ............... | A61H 7/005 604/116 |
| 2015/0065916 | A1 * | 3/2015 | Maguire .......... | A61B 5/150748 600/573 |
| 2016/0136362 | A1 * | 5/2016 | Tromborg ............. | A61M 5/425 604/115 |
| 2017/0274158 | A1 | 9/2017 | Saeed Malik | |
| 2017/0333074 | A1 | 11/2017 | Clark, III et al. | |
| 2018/0338812 | A1 * | 11/2018 | Morey ............... | A61B 17/3403 |
| 2020/0054378 | A1 * | 2/2020 | Kincaid ................... | A61B 6/12 |
| 2020/0230366 | A1 | 7/2020 | Spataro et al. | |
| 2022/0031211 | A1 * | 2/2022 | Yakhnich ........... | A61B 5/15113 |

FOREIGN PATENT DOCUMENTS

| | | |
|---|---|---|
| JP | H10512177 A | 11/1998 |
| JP | 2006521886 A | 9/2006 |
| JP | 2017514577 A | 6/2017 |
| WO | 2011/019985 | 2/2011 |
| WO | 2014197625 A1 | 12/2014 |
| WO | 2016091956 A1 | 6/2016 |
| WO | 2019232414 A1 | 12/2019 |

* cited by examiner

IV CATHETER INSERTION GUIDE

RELATED APPLICATIONS

This application claims benefit of U.S. Provisional Patent Application No. 63/107,342, filed on Oct. 29, 2020, entitled IV CATHETER INSERTION GUIDE FOR REDUCING PAIN, which is incorporated herein in its entirety.

BACKGROUND

Intravenous (IV) catheter devices are commonly used for a variety of infusion therapies. For example, an IV catheter device may be used for infusing fluids, such as normal saline solution, various medicaments, and total parenteral nutrition, into a patient. IV catheter devices may also be used for withdrawing blood from the patient.

A common type of IV catheter device is an over-the-needle peripheral intravenous ("IV") catheter ("PIVC"). As its name implies, the over-the-needle catheter may be mounted over a needle having a sharp distal tip. The catheter and the needle may be assembled so that the distal tip of the needle extends beyond the distal tip of the catheter with the bevel of the needle facing up away from skin of the patient. The catheter and needle are generally inserted at a shallow angle through the skin into the vasculature of the patient. The process of inserting the catheter and needle through the patient's skin and into the vasculature can be painful and even frightening for some patients.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to an IV catheter insertion guide that is configured to reduce the pain a patient may experience during catheter insertion. The IV catheter insertion guide may include two platforms that can be positioned on opposing sides of the insertion site. An upstream platform can include an ultrasonic transducer or another type of heating component for increasing the temperature of tissue near the insertion site. This heating of the tissue can cause the targeted vessel to relax and increase its cross-sectional area prior to insertion of the catheter. A downstream platform can also include an ultrasonic transducer for stimulating nerves downstream from the insertion site during the insertion of the catheter. The stimulation of the downstream nerves may reduce the pain signal that is transmitted to the central nervous system in response to the catheter insertion.

The upstream platform may also include various angled surfaces or components that can act as guides for the insertion of the catheter. The upstream platform may further include a light source for illuminating the insertion site to thereby provide better contrast between the targeted vessel and the surrounding tissue. Accordingly, an IV catheter insertion guide configured in accordance with embodiments of the present disclosure can simplify the insertion process while also reducing the pain or discomfort the patient may feel.

In some embodiments, an IV catheter insertion guide may include an upstream platform and a downstream component. The upstream component may be configured to be positioned on a patient's skin on an upstream side of a planned insertion site. The downstream platform may be configured to be positioned on the patient's skin on a downstream side of the planned insertion site opposite the upstream platform. The downstream platform may include a nerve stimulating component for stimulating nerves downstream from the planned insertion site.

In such embodiments, the upstream platform may include a heating component for heating tissue around the planned insertion site. The heating component may be an ultrasonic transducer. In some embodiments, the upstream platform may include a light source. The upstream platform may comprise a main body having an inwardly curved front and the light source may comprise a near infrared light bar that extends along the inwardly curved front.

In some embodiments, the upstream platform may comprise a main body having a top that forms a first angled support surface that is configured to support a catheter device at a first angle. In such embodiments, the upstream platform may comprise an elevated support structure that forms a second angled support surface that is configured to support a catheter device at a second angle. The second angle may be greater than the first angle. The main body may include a channel in which a coupling element of the elevated support structure is moveable to reposition the elevated support structure.

In some embodiments, the nerve stimulating component of the downstream platform may be an ultrasonic transducer. In some embodiments, the upstream platform and the downstream platform may be configured to be secured to the patient's skin. Each of the upstream platform and the downstream platform may include an adhesive or a strap by which the respective platform is secured to the patient's skin.

In some embodiments, an IV catheter insertion guide may include an upstream platform having a heating component for heating tissue around an insertion site, a light source for emitting light on the insertion site and one or more angled support surfaces for supporting a catheter device while a catheter of the catheter device is inserted at the insertion site. The IV catheter insertion guide may also include a downstream platform that includes a nerve stimulating component for stimulating nerves downstream from the insertion site. In such embodiments, the nerve stimulating component may be an ultrasonic transducer.

In such embodiments, the one or more angled support surfaces may comprise a first angled support surface formed on a main body of the upstream platform and a second angled support surface formed on an elevated support structure that is coupled to the main body. The elevated support structure may be repositionable relative to the main body.

In some embodiments, a method for reducing pain at a procedure site may include: positioning an upstream platform and a downstream platform on opposing sides of the procedure site; prior to performing the procedure, activating a nerve stimulating component in the downstream component; and while the nerve stimulating component is activated, performing the procedure. In some embodiments, the method may also include, prior to performing the procedure, activating a heating component in the upstream platform. In some embodiments, the method may also include, prior to performing the procedure, activating a light source on the upstream platform.

It is to be understood that both the foregoing general description and the following detailed description are examples and explanatory and are not restrictive of the invention, as claimed. It is to be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the accompanying drawings in which.

DESCRIPTION OF EMBODIMENTS

Figure 1:
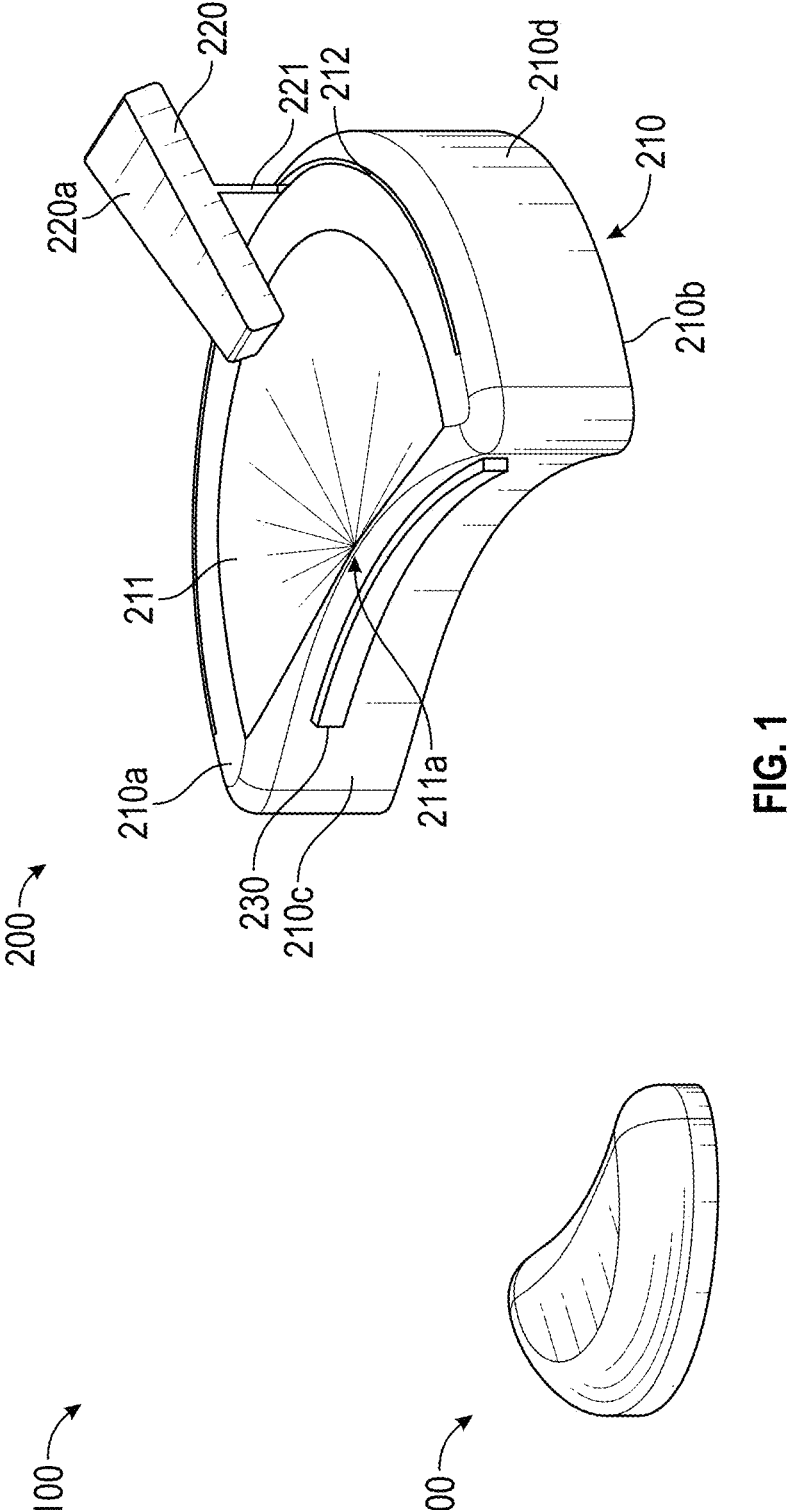
FIG. 1 illustrates an example of an IV catheter insertion guide that includes an upstream platform and a downstream platform in accordance with one or more embodiments.
Figure 2A:
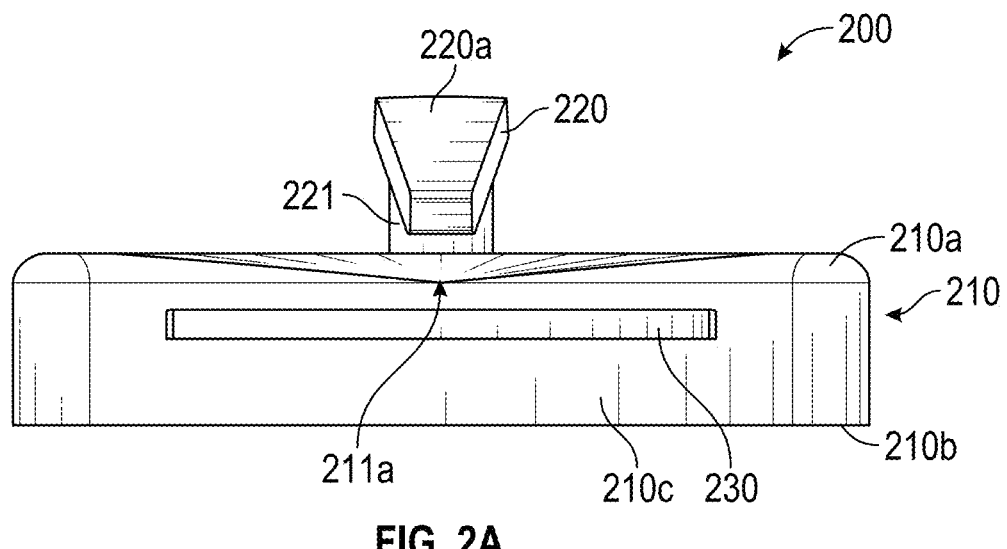
FIG. 2A is a front view of the upstream platform of the IV catheter insertion guide illustrated in FIG. 1.
Figure 2B:
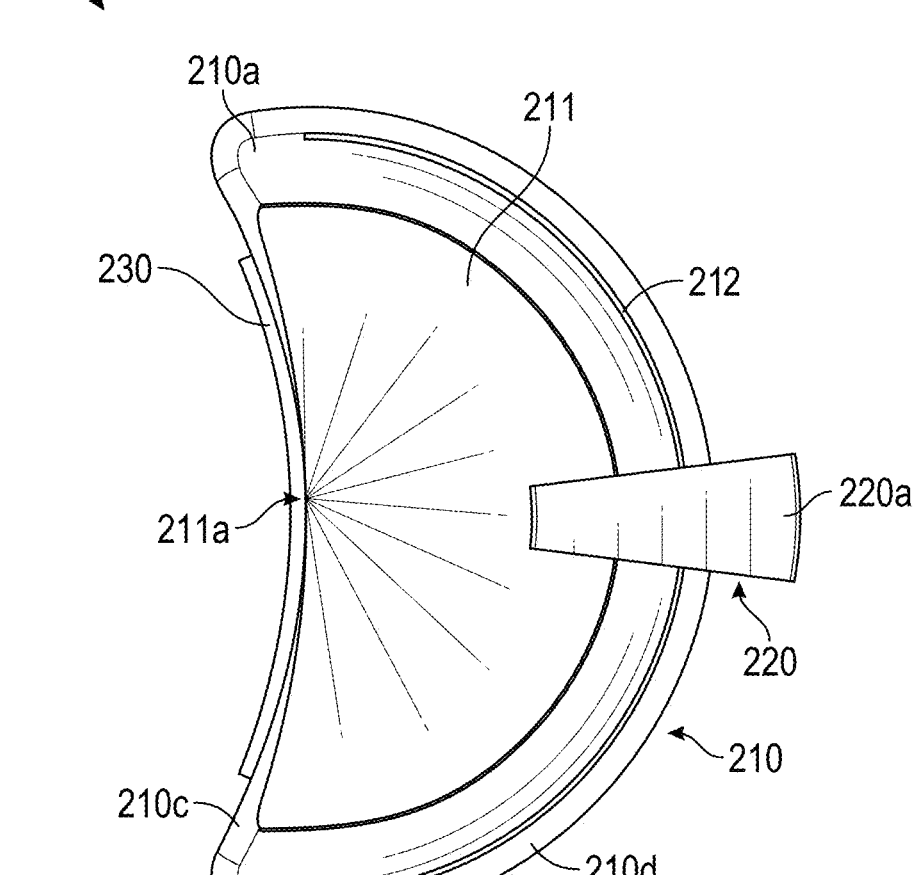
FIG. 2B is a top view of the upstream platform of the IV catheter insertion guide illustrated in FIG. 1.
Figure 2C:
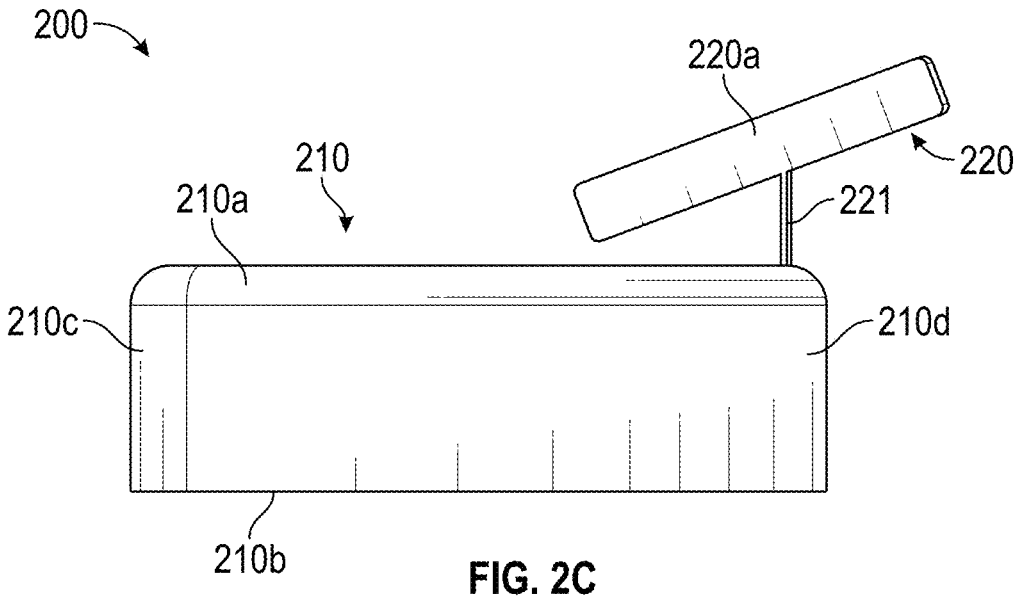
FIG. 2C is a side view of the upstream platform of the IV catheter insertion guide illustrated in FIG. 1.
Figure 2D:
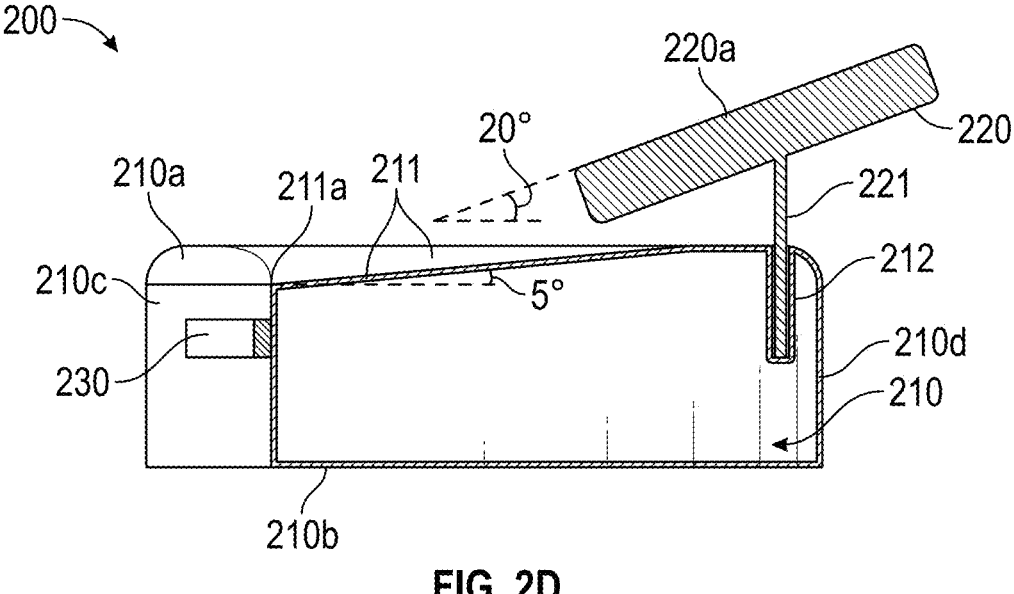
FIG. 2D is a cross-sectional side view of the upstream platform of the IV catheter insertion guide illustrated in FIG. 1.
Figure 3A:
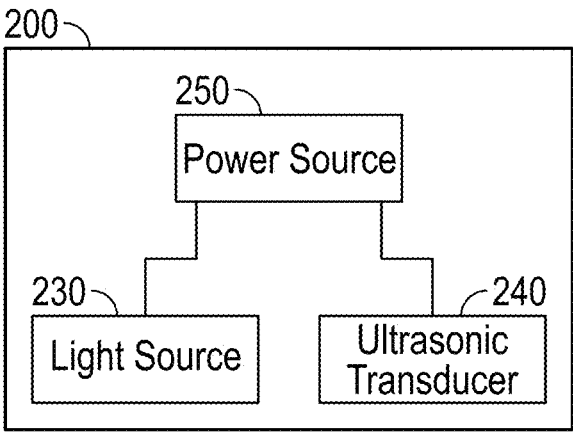
FIG. 3A is a block diagram representing circuitry that may be included in the upstream platform of the IV catheter insertion guide illustrated in FIG. 1.
Figure 3B:
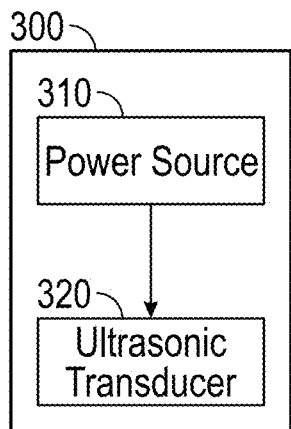
FIG. 3B is a block diagram representing circuitry that may be included in the downstream platform of the IV catheter insertion guide illustrated in FIG. 1.

FIG. 1 provides an example of an IV catheter insertion guide 100 that is configured in accordance with one or more embodiments of the present disclosure. IV insertion guide 100 includes an upstream platform 200 and a downstream platform 300. FIGS. 2A-2D provide additional views of upstream platform 200, while FIGS. 3A and 3B illustrate circuitry that may be included in upstream platform 200 and downstream platform 300 respectively. In this context, the terms "upstream" and "downstream" reference the direction that blood flows in the vessel. Accordingly, when IV catheter insertion guide 100 is used to insert a catheter into a vein in a patient's arm, upstream platform 200 would typically be positioned on the distal side of the insertion site (i.e., towards the hand) while downstream platform 300 would typically be positioned on the proximal side of the insertion site. However, embodiments of the present disclosure should not be limited by how upstream platform 200 and downstream platform 300 may be positioned. As such, the terms "upstream" and "downstream" may be viewed as only distinguishing between the two platforms.

Upstream platform 200 includes a main body 210 that includes a top 210a, a bottom 210b, a front 210c and a rear 210d. In the depicted embodiment, main body 210 has a general crescent shape but it could have any other suitable shape. Bottom 210b is intended to be placed on the patient's skin and may therefore be flat or curved to match the contour of the patient's body (e.g., the contour of the forearm). A first angled support surface 211 may be formed in top 210a. As shown in the depicted embodiment, first angled support surface 211 may be in the shape of a partial, inverted cone having an apex 211a positioned at front 210c. However, other shapes and configurations of first angled support surface 211 could also be employed. Accordingly, first angled support surface 211 may represent any angled surface in top 210a that is angled downwardly towards and extends to front 210c. A channel 212 may also be formed in top 210a or possibly along rear 210d. Channel 212 may extend around top 210a along a portion or all of rear 210d. Accordingly, channel 212 may have a curved or semi-circular shape.

Upstream platform 200 may also include an elevated support structure 220 that is coupled to main body 210 via a coupling element 221. Elevated support structure 220 may form a second angled support surface 220a that is elevated above first angled support surface 211. In some embodiments, coupling element 221 may be configured to slide along channel 212 to thereby allow the position of second angled support surface 220a relative to main body 210 to be adjusted. In some embodiments, coupling element 221 may be configured to move in to and out from channel 212 to thereby allow the height of second angled support surface 220a relative to main body 210 to be adjusted. In some embodiments, coupling element 221 may be removable from channel 212 to thereby allow elevated support structure 220 to be detached from main body 210. In some embodiments, upstream platform 200 may not include elevated support structure 220, in which case main body may not include channel 212.

Both first angled support surface 211 and second angled support surface 220a can be used to support an IV catheter device while inserting the catheter. As shown in FIG. 2D, second angled support surface 220a may have a greater angle (e.g., 20°) than first angled support surface 211 (e.g., 5°) relative to bottom 210b and therefore relative to the patient's skin. These different angles can simplify the catheter insertion process. For example, a clinician may initially position the IV catheter device on second angled support surface 220a to pierce through the skin at a sharper angle and may then position the IV catheter device on first angled support surface 211 to advance the catheter through the vessel at a narrower angle. In the depicted embodiment, the curved shape of channel 212 matches the conical shape of first angled support surface 211. As a result, second angled support surface 220a will be oriented towards apex 211a regardless of where elevated support structure 220 may be positioned within channel 212.

Upstream platform 200 also includes a light source 230 that is positioned on front 210 c where it can illuminate the skin surrounding the insertion site. Light source 230 may emit near infrared light to thereby provide enhanced contrast between the vessels and the surrounding tissue and skin. In the depicted embodiment, front 210 c has a concave (or inwardly curved) shape and light source 230 is in the form of a light bar that extends across front 210 c. In such embodiments, the light emitted by light source 230 will be concentrated around the insertion site. In some embodiments, light source 230 may also or alternatively be positioned on bottom 210 b to thereby emit near infrared light directly into the skin beneath main body 210.

As shown in FIG. 3A, upstream platform 200 can also include an ultrasonic transducer 240 that is configured to emit ultrasonic waves into the tissue below and around upstream platform 200. These ultrasonic waves can warm the skin and tissue around the target vessel thereby causing the vessel wall to relax. The relaxing of the vessel wall can increase the cross-sectional area of the vessel making it easier to insert the catheter into the vessel. In some embodiments, another type of heating component other than an ultrasonic transducer may be used to warm the tissue including, for example, a heating coil or a near infrared light.

Upstream platform 200 may also include a power source 250 that may be used to power light source 230 and ultrasonic transducer 240 (or another heating component). In some embodiments, power source 250 may be a rechargeable battery, while in other embodiments, power source 250 may represent an external source of power.

As shown in FIG. 3B, downstream component 300 may also include an ultrasonic transducer 320 (or other "nerve stimulating component"). Unlike ultrasonic transducer 240, which is primarily intended to heat the tissue surrounding the insertion site, ultrasonic transducer 320 is primarily intended to use ultrasound to stimulate nerves that are downstream from the insertion site (i.e., nerves that are towards the central nervous system from the insertion site). Downstream component 300 may include a power source 310 for powering ultrasonic transducer 320. Power source 310 could be separate from power source 250 in some embodiments (e.g., two separate batteries), or may be the same in other embodiments (e.g., an external power source that powers the components in downstream platform 200 and upstream platform 300).

Figure 4A:
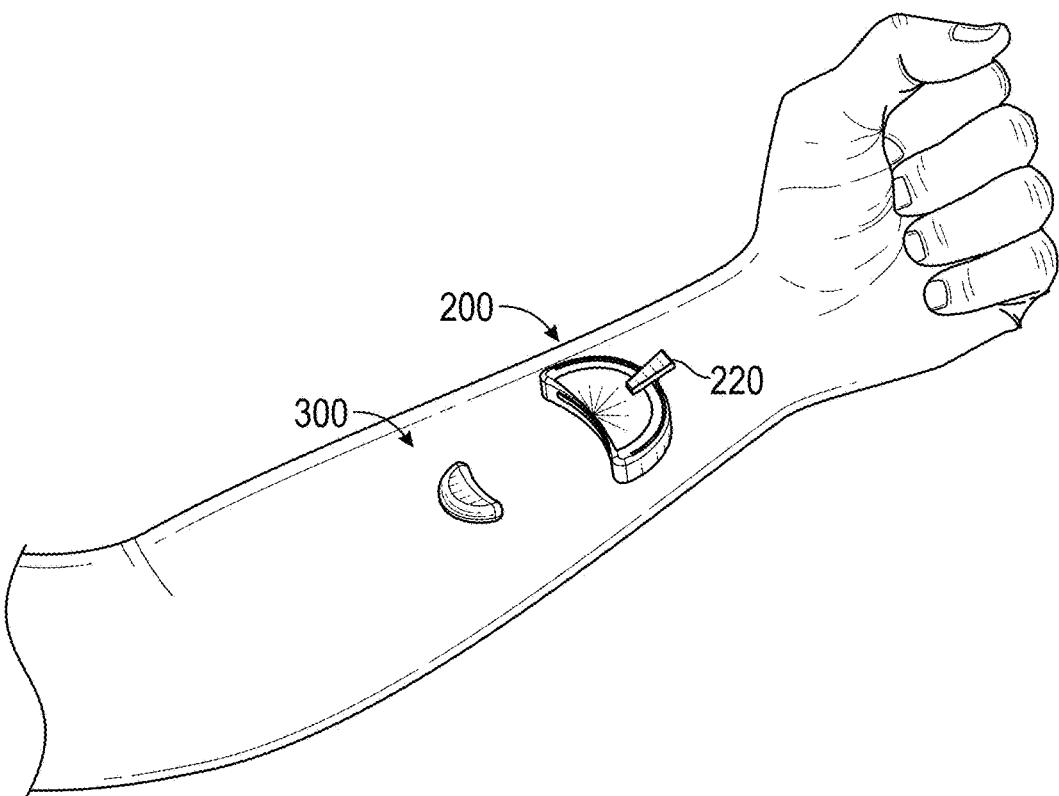
FIGS. 4A-4D provide an example of how the IV catheter insertion guide of FIG. 1 may be used.

FIGS. 4A-4D provide an example of how IV catheter insertion guide 100 may be used. In FIG. 4A, upstream platform 200 and downstream platform 300 are shown as being placed on a patient's forearm. Upstream platform 200 and downstream platform 300 can be positioned on opposing sides of the planned insertion site. Upstream platform 200 can be positioned distal to downstream platform 300 and can be oriented so that front 210a faces towards downstream platform 300. In some embodiments, bottom surface 201b of upstream platform 200 and the bottom surface of downstream platform 300 may include an adhesive or a suction device, or each platform may include a strap or some other structure or material for securing the platforms to the skin so that the clinician need not hold either platform in place. In other embodiments, both upstream platform and downstream platform 300 may be integrated into the same sleeve, sheet or other material that can be positioned on or around the patient's arm.

With upstream platform 200 and downstream platform 300 in place on opposing sides of the planned insertion site, a clinician may activate ultrasonic transducer 240 and ultrasonic transducer 320. In some embodiments, the clinician may activate ultrasonic transducer 240 prior to preparing the IV catheter device so that the skin and tissue will be heated sufficiently once the IV catheter device is ready to be used. On the other hand, the clinician may not activate ultrasonic transducer 320 until he or she is about to insert the catheter. Accordingly, the timing of activating ultrasonic transducer 240 or ultrasonic transducer 320 is not essential.

Figure 4B:
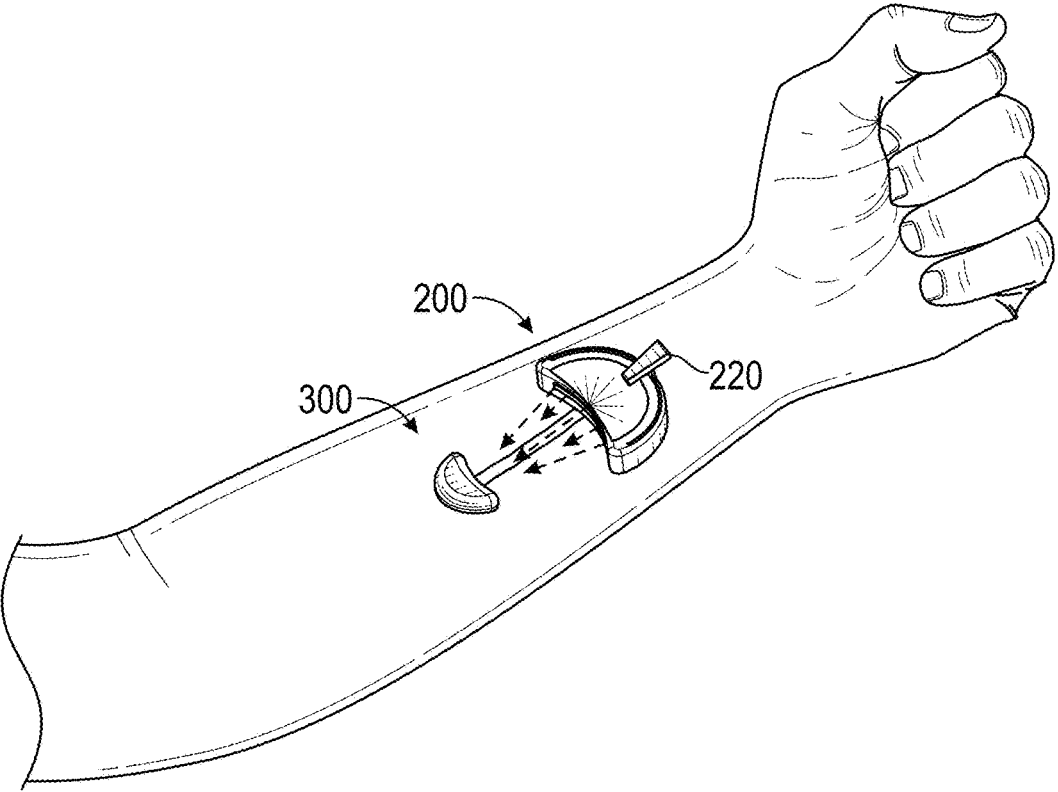

Turning to FIG. 4B, it is assumed that the clinician is ready to insert the catheter, and therefore the clinician has activated light source 230 to cause the skin surrounding the planned insertion site to be illuminated. As described above, light source 230 may emit near infrared light which can cause the vessels around the planned insertion site to appear with greater contrast.

Figure 4C:
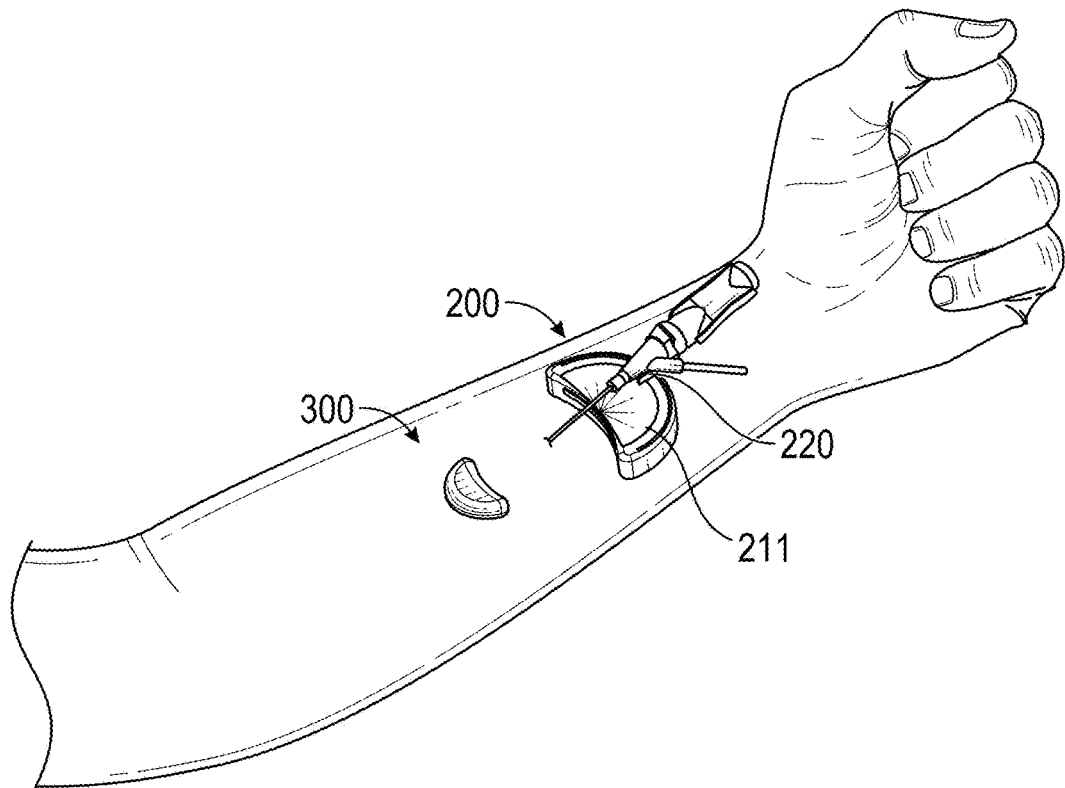

Turning to FIG. 4C, the clinician may position the IV catheter device on second angled surface 220a of elevated support structure 220 to cause the needle and catheter to be oriented at a sharp angle towards the skin (e.g., 20°). In this orientation, the clinician may puncture the skin and commence inserting the needle and catheter. Notably, at this step, ultrasonic transducer 320 can be activated so that the nerves downstream of the insertion site will be stimulated during the insertion. It is believed that, based on gate control theory, the stimulation of the downstream nerves will reduce the downstream nerves' ability to relay pain signals that are generated at the insertion site to the central nervous system. As a result, the patient may feel a weak sensation as opposed to sharp pain as the needle and catheter are inserted.

Figure 4D:
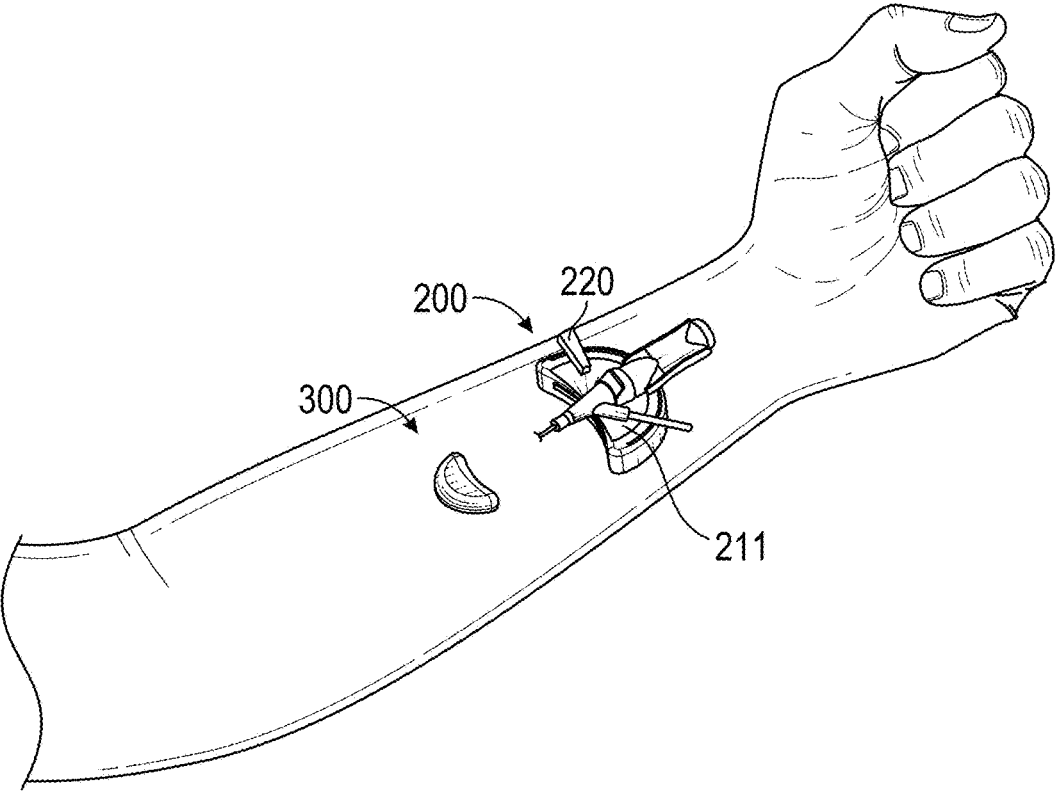

Turning to FIG. 4D, the clinician may position the IV catheter device on first angled surface 211 and complete the insertion process at the shallower angle (e.g., 5°). To do so, the clinician may slide elevated support structure 220 within or remove it from channel 212 to allow the IV catheter device to be moved directly downward onto first angled surface 211. However, in some cases, the clinician may move the IV catheter device rather than moving elevated support structure 220.

In the above-described examples, upstream platform 200 and downstream platform 300 form part of an IV catheter insertion guide. However, in some embodiments, similarly configured upstream and downstream platforms may perform similar functions for other types of procedures. For example, the upstream and downstream platforms could be positioned on opposing sides of a burn to be treated, a cut to be sutured, a mole or skin growth to be removed or any other location on the skin where a potentially painful procedure may be performed. In such cases, the ultrasonic transducer in the downstream platform may be activated to reduce the downstream nerves' ability to transmit pain signals to the central nervous system during the procedure. Similarly, the upstream platform may provide a guide for any instruments used during the procedure, near infrared or other light for illuminating the site of the procedure and/or heating for the surrounding tissue.

All examples and conditional language recited herein are intended for pedagogical objects to aid the reader in understanding the present disclosure and the concepts contributed by the inventor to furthering the art and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed:

1. An IV catheter insertion guide comprising:
   an upstream platform that is configured to be positioned on a patient's skin on an upstream side of a planned insertion site; and
   a downstream platform that is configured to be positioned on the patient's skin on a downstream side of the planned insertion site opposite the upstream platform, the downstream platform including a nerve stimulating component for stimulating nerves downstream from the planned insertion site,
   wherein the upstream platform comprises a main body having a top that forms a first angled support surface in a shape of a partial, inverted cone having an apex, wherein the main body of the upstream platform further comprises an inwardly curved front, wherein the apex is positioned at the inwardly curved front, wherein the first angled support surface is configured to support a catheter device at a first angle, wherein the upstream platform further comprises an elevated support structure that forms a second angled support surface that is configured to support a catheter device at a second angle, wherein the elevated support structure is configured to slide from a first position to a second position, wherein the elevated support structure is oriented towards the apex when the elevated support structure is in the first position and the second position.

2. The IV catheter insertion guide of claim 1, wherein the upstream platform includes a heating component for heating tissue around the planned insertion site.

3. The IV catheter insertion guide of claim 2, wherein the heating component is an ultrasonic transducer.

4. The IV catheter insertion guide of claim 1, wherein the upstream platform comprises a light source.

5. The IV catheter insertion guide of claim 4, wherein the light source comprises a near infrared light bar that extends along the inwardly curved front.

6. The IV catheter insertion guide of claim 1, wherein the second angle is greater than the first angle.

7. The IV catheter insertion guide of claim 1, wherein the nerve stimulating component is an ultrasonic transducer.

8. The IV catheter insertion guide of claim 1, wherein the upstream platform and the downstream platform are configured to be secured to the patient's skin.

9. The IV catheter insertion guide of claim 8, wherein each of the upstream platform and the downstream platform include an adhesive or a strap by which the respective platform is secured to the patient's skin.

10. The IV catheter insertion guide of claim 1, wherein the main body of the upstream platform comprises a channel, wherein the elevated support structure is configured to slide from the first position to the second position via a coupling element disposed within the channel.

11. The IV catheter insertion guide of claim 10, wherein the channel is semi-circular.

12. An IV catheter insertion guide comprising:

an upstream platform that is configured to be positioned on a patient's skin on an upstream side of a planned insertion site, wherein the upstream platform comprises a main body and an elevated support structure, wherein the main body comprises a top that forms a first angled support surface in a shape of a partial cone, wherein the partial cone is inverted and comprises an apex, wherein the first angled support surface is configured to support a catheter device at a first angle, wherein the elevated support structure forms a second angled support surface configured to support the catheter device at a second angle, wherein the main body of the upstream platform comprises a semi-circular channel, wherein the main body of the upstream platform comprises a semi-circular channel formed in the top, wherein the elevated support structure is configured to slide from a first position to a second position within the channel; wherein the second angled support surface is oriented towards the apex when the elevated support structure is in the first position and the second position within the channel; and a downstream platform that includes a nerve stimulating component for stimulating nerves downstream from the insertion site.

13. The IV catheter insertion guide of claim 12, wherein the nerve stimulating component is an ultrasonic transducer.

14. The IV catheter insertion guide of claim 12, wherein the elevated support structure is repositionable relative to the main body.

15. The IV catheter insertion guide of claim 12, wherein the upstream platform further comprises a coupling element coupling the elevated support structure to the main body, wherein the main body of the upstream platform comprises a channel, wherein the coupling element is configured to slide within the channel, wherein the coupling element is removable from the channel to detach from the main body.

16. The IV catheter insertion guide of claim 15, wherein the channel is semi-circular.

* * * * *